US008044233B2

(12) United States Patent
Staffel et al.

(10) Patent No.: US 8,044,233 B2
(45) Date of Patent: Oct. 25, 2011

(54) PROCESS FOR PREPARING VINYL CARBOXYLATES

(75) Inventors: Wolfgang Staffel, Heidelberg (DE); Roland Kessinger, Weinheim (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 625 days.

(21) Appl. No.: 12/092,222

(22) PCT Filed: Nov. 22, 2006

(86) PCT No.: PCT/EP2006/068756
§ 371 (c)(1),
(2), (4) Date: Apr. 30, 2008

(87) PCT Pub. No.: WO2007/060176
PCT Pub. Date: May 31, 2007

(65) Prior Publication Data
US 2008/0308765 A1    Dec. 18, 2008

(30) Foreign Application Priority Data

Nov. 23, 2005  (DE) .................. 10 2005 055 852
Jun. 14, 2006  (DE) .................. 10 2006 027 698
Sep. 28, 2006  (DE) .................. 10 2006 046 112

(51) Int. Cl.
C07C 67/04  (2006.01)
C07C 227/18  (2006.01)

(52) U.S. Cl. ..................................... 560/242

(58) Field of Classification Search ........................ None
See application file for complete search history.

(56) References Cited

U.S. PATENT DOCUMENTS

| 2,066,075 A | 12/1936 | Reppe et al. |
| 3,008,979 A | 11/1961 | Wilip et al. |
| 3,455,998 A | 7/1969 | Arpe et al. |
| 3,607,915 A | 9/1971 | Borsboom et al. |
| 5,300,403 A | 4/1994 | Angelopolus et al. |
| 5,430,179 A | 7/1995 | Lincoln et al. |
| 6,261,813 B1 * | 7/2001 | Khmelnitsky et al. ........ 435/135 |

FOREIGN PATENT DOCUMENTS

| EP | 0 512 656 | 11/1992 |
| GB | 827718 | 2/1960 |
| GB | 1134362 | 11/1968 |
| JP | 2006-28280 | 2/2006 |

OTHER PUBLICATIONS

Feiring et al. Journal of Fluorine Chemistry, 2002, 118, 95-98.*
Usyatinsky et al Biotechnology and Bioengineering, 2003, 82(4), 379-385.*
U.S. Appl. No. 12/598,934, filed Nov. 5, 2009, Tishkov, et al.
Ruimao Hua et al., J. Org. Chem. 2004, 69, pp. 5782-5784.
Mueller et al., "Developing Transition metal Catalysts for the Intrmolecular Hydroamination of Alkynes" A Organometallics 2000, 19, pp. 170-183.
Hopff et al., "Zur Kenntnis der aromatischen Vinylester" Makromolekulare Chemie 18/19 (1956), pp. 227-238.
Database CA Online]; Ooka, Masataka, et al., "Curable, weather-resistant fluoropolymer compositions" STN Database accession No. 1987:638719 & JP62185740A.
Database CA [Online]; Takata, Atsumu et al., "Vinylpolymerization. CVI. Preparation and polymerization of vinyl bicyclo [2.2.2] octane-2-carboxylate" STN Databses accession No. 1976:116015 &Kogyo Kagaku Zasshi, 68(6), 1129-31.
Database CA [Online]: Motoki, Kenji: "Divinyl dicarboxylate ester polymers" STN Database accession No. 1976:447520 & JP49061275A.
Database CA [Online]; Blokhin, V.E. et al.: "Synthesis of unsatured esters of pyridine- and quinoline dicarboxylic acids" STN Database accession No. 1970:90227 & Khimiya Geterotsiklicheskikh Soedinenii, 1969 (4), 744-5.
Ye et, al.: "Synthesis and structure of some ruthenium-rhenium heterodinuclear complexes and their catalytic activity in the addition of carboxylic acids to phenylacetylene" Journal of Organometallic Chemistry, vol. 691, No. 6, 1216-1222, 2006.
Database CA Online]: "Polybasic carboxylic acid alkenyl esters" STN Database accession No. 1981: 46797 & JP55104229A.
U.S. Appl. No. 12/446,460, filed Apr. 21, 2009, Boehling, et al.
Larry J. Loeffler, et al., "Antineoplastic Agents. 2. Structure-Activity Studies on N-Protected Vinyl, 1,2-Dibromoethyl, and Cyanomethyl Esters of Several Amino Acids", Journal of Medicinal Chemistry, vol. 20, No. 12, 1977, pp. 1584-1588.

* cited by examiner

Primary Examiner — Daniel Sullivan
Assistant Examiner — Yevegeny Valenrod
(74) Attorney, Agent, or Firm — Oblon, Spivak, McClelland, Maier & Neustadt, L.L.P.

(57) ABSTRACT

The present invention relates to a process for preparing vinyl carboxylates, wherein a carboxylic acid is reacted with an alkyne compound in the presence of a catalyst which is selected from carbonyl complexes, halides and oxides of rhenium, of manganese, of tungsten, of molybdenum, of chromium and of iron and rhenium metal at a temperature of $\leq 300°$ C.

The process gives the desired vinyl esters with high yield.

30 Claims, No Drawings

PROCESS FOR PREPARING VINYL CARBOXYLATES

The present invention relates to a process for preparing vinyl carboxylates by reacting a carboxylic acid with an alkyne.

The addition of carboxylic acids to alkynes to prepare the corresponding vinyl carboxylates has been known for some time. Suitable catalysts used are especially zinc salts, such as the zinc salt of the carboxylic acid taking part in the reaction; see, for example, U.S. Pat. No. 2,066,075, U.S. Pat. No. 3,455,998 and U.S. Pat. No. 3,607,915.

Since the zinc salts have only low selectivity and stability, attempts have been made to use other catalysts. For instance, U.S. Pat. No. 5,430,179 describes the use of ruthenium complexes soluble in the reaction medium with a phosphine ligand. EP 512 656 A describes a process for preparing vinyl derivatives of Brønsted acids, such as carboxylic acids, by reacting the Brønsted acid with an acetylenically unsaturated compound in the presence of a ruthenium catalyst which is applied to an inter porous support. J. Org. Chem. 2004, 69, 5782-5784 describes the reaction of terminal alkynes with acetic acid or benzoic acid using $Re(CO)_5Br$ as the catalyst. It has been found that the anti-Markovnikov adduct is obtained with high selectivity especially in n-heptane and toluene as solvents. Organometallics 2000, 19, 170-183 describes the intramolecular hydroamination of aminoalkyne compounds using $[Re(CO)_5(H_2O)]BF4$ as a catalyst. However, only a low yield is obtained.

It is common to the prior art process that the yield of vinyl esters is not satisfactory.

It is therefore an object of the present invention to provide a process for preparing vinyl carboxylates which proceeds with high yield.

Moreover, the process shall be performable at temperatures at which even the thermally labile carboxylic acids and vinyl carboxylates do not decompose.

Finally, the process shall be performable with small amounts of catalyst in order to restrict the costs for the catalyst.

It has now been found that, surprisingly, this object is achieved when the catalyst used is a carbonyl complex, a halide or oxide of rhenium, of manganese, of tungsten, of molybdenum, of chromium, of iron or rhenium metal.

The present invention therefore provides a process for preparing vinyl carboxylates of the formula I:

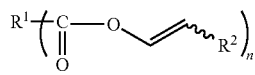
(I)

in which
a) $R^1$ is H or —COO—CH=CH—$R^2$ and n is 1, or
b) $R^1$ is $C_1$-$C_{20}$-alkyl, $C_2$-$C_{20}$-alkenyl, $C_3$-$C_7$-cycloalkyl, and n is 1, 2, 3 or 4, where $R^1$ is optionally substituted by 1, 2 or 3 radicals which are each independently selected from phenyl, halogen, hydroxy, $C_1$-$C_4$-alkoxy, amino, mono-$C_1$-$C_4$-alkyl-amino, di-$C_1$-$C_4$-alkylamino, —$OCOR^3$, —$COOR^3$, —$CONR^4$, $R^5$, —$NR^4COR^5$, —$OCONR^4R^5$ or —$NR^4COOR^5$, or
c) $R^1$ is aryl and n is 1, 2, 3, 4, 5 or 6, where aryl is optionally substituted by 1, 2 or 3 radicals which are independently selected from $C_1$-$C_4$-alkyl, halogen, hydroxy $C_1$-$C_4$-alkoxy, amino, mono-$C_1$-$C_4$-alkylamino, di-$C_1$-$C_4$-alkylamino, —$OCOR^3$, —$COOR^3$, —$CONR^4R^5$, —$NR^4COR^5$, —$OCONR^4R^5$ or —$NR^4COOR^5$, or
d) $R^1$ is bicycloalkyl having from 6 to 9 or from 7 to 9 carbon atoms or bicycloalkenyl having from 6 to 9 or from 7 to 9 carbon atoms and one or two carbon-carbon double bonds, and n is 1 or 2, where the bicycloalkyl radical may be substituted by 1, 2, 3, 4, 5 or 6 radicals which are each independently selected from halogen or $C_1$-$C_4$-alkyl, or
e) $R^1$ is five- or six-membered heterocyclyl which has one or two heteroatoms which are each independently selected from N, O and S, and n is 1, 2 or 3, where the heterocyclyl radical may be substituted by 1 or 2 radicals which are each independently selected from halogen or $C_1$-$C_4$-alkyl;

$R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl;

$R^3$ is $C_1$-$C_4$-alkyl;

$R^4$ and $R^5$, which may be the same or different, are each H or $C_1$-$C_4$-alkyl; comprising the reaction of a compound of the formula II

(II)

in which $R^1$ is H, —COOH or as defined above under b) or c) and n is as defined above with a compound of the formula III

(III)

in which $R^2$ is as defined above, in the presence of a catalyst which is selected from carbonyl complexes, oxides and halides of rhenium, of manganese, of tungsten, of molybdenum, of chromium and of iron and rhenium metal at a temperature of $\leq 300°$ C.

A preferred embodiment of the present invention is a process for preparing vinyl carboxylate compounds of the formula I:

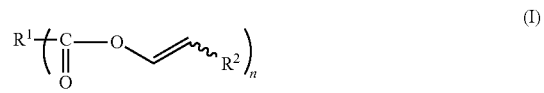
(I)

in which
a) $R^1$ is H or —COO—CH=CH—$R^2$ and n is 1,
b) $R^1$ is $C_1$-$C_{20}$-alkyl, $C_2$-$C_{20}$-alkenyl, $C_3$-$C_7$-cycloalkyl, and n is 1, 2, 3 or 4, in particular 1, 2 or 3, where $R^1$ is optionally substituted by 1 or 2 radicals which are each independently selected from phenyl, halogen, hydroxy, $C_1$-$C_4$-alkoxy, amino, mono-$C_1$-$C_4$-alkylamino, di-$C_1$-$C_4$-Alkylamino, —$OCOR^3$, —$COOR^3$, —$CONR^4R^5$, —$NR^4COR^5$, —$OCONR^4R^5$ or —$NR^4COOR^5$, or
c) $R^1$ is aryl and n is 1, 2, 3, 4, 5 or 6, where aryl is optionally substituted by 1, 2 or 3 radicals which are each independently selected from $C_1$-$C_4$-alkyl, halogen, hydroxy $C_1$-$C_4$-alkoxy, amino, mono-$C_1$-$C_4$-alkylamino, di-$C_1$-$C_4$-alkylamino, —$OCOR^3$, —$COOR^3$, —$CONR^4R^5$, —$NR^4COR^5$, —$OCONR^4R^5$ or —$NR^4COOR^5$, or $R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl;

$R^3$ is $C_1$-$C_4$-alkyl;

$R^4$ and $R^5$, which may be the same or different, are each H or $C_1$-$C_4$-alkyl;

comprising the reaction of a compound of the formula II

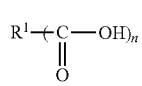  (II)

in which $R^1$ is H, —COOH or as defined above under b) or c) and n is as defined above with a compound of the formula III

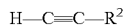  (III)

in which $R^2$ is as defined above, in the presence of a catalyst which is selected from carbonyl complexes, oxides and halides of rhenium, of manganese, of tungsten, of molybdenum, of chromium and of iron at a temperature of $\leq 300°$ C., preferably $\leq 260°$ C., in particular $\leq 230°$ C.

In a further preferred embodiment, the invention relates to a process for preparing vinyl carboxylate compounds of the formula I:

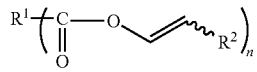  (I)

in which
a) $R^1$ is H or —COO—CH=CH—$R^2$ and n is 1,
b) $R^1$ is $C_1$-$C_{20}$-alkyl, $C_2$-$C_{20}$-alkenyl, $C_3$-$C_7$-cycloalkyl, and n is 1, 2, 3 or 4, in particular 1, 2 or 3, where $R^1$ is optionally substituted by 1 or 2 radicals which are each independently selected from phenyl, halogen and $C_1$-$C_4$-alkoxy or
c) $R^1$ is aryl and n is 1, 2, 3, 4, 5 or 6, where aryl is optionally substituted by 1, 2 or 3 radicals which are each independently selected from $C_1$-$C_4$-alkyl, halogen and $C_1$-$C_4$-alkoxy;
$R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl;
by reacting a compound of the formula II

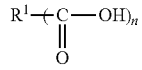  (II)

in which $R^1$ is H, —COOH or as defined above under b) or c) and n is as defined above with a compound of the formula III

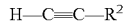  (III)

in which $R^2$ is as defined above, in the presence of a catalyst which is selected from carbonyl complexes of rhenium, of manganese, of tungsten, of molybdenum, of chromium and of iron at a temperature of $\leq 300°$ C., preferably $\leq 260°$ C., in particular $\leq 230°$ C.

The alkyl groups may be straight-chain or branched alkyl groups having the carbon number specified. Examples of such alkyl groups are methyl, ethyl, n-propyl, i-propyl, n-butyl, i-butyl, sec-butyl, t-butyl, n-hexyl, n-dodecyl, etc.

Examples of $C_2$-$C_{20}$-alkenyl groups are vinyl, 1- or 2-propenyl, buten-1-yl, buten-2-yl and isobutenyl.

Halogen means fluorine, chlorine, bromine or iodine.

Examples of $C_3$-$C_7$-cycloalkyl groups are cyclopropyl, cyclobutyl, cycloheptyl and especially cyclopentyl and cyclohexyl.

Examples of bicycloalkyl groups are bicyclo[2.1.1]hexane, bicyclo[2.2.1]heptane, bicyclo[2.2.2]octane and bicyclo[2.3.2]nonane.

Examples of bicycloalkenyl groups are bicyclo[2.2.1]heptene, bicyclo[2.2.2]octene and bicyclo[2.3.2]nonene.

Heterocyclyl may be aromatic or saturated or unsaturated nonaromatic heterocyclyl.

Examples of aromatic heterocyclyl are pyridyl, pyrimidyl, triazinyl, pyrrolyl, furyl, thienyl, oxazolyl, isooxazolyl, thiazolyl, isothiazolyl, imidazolyl, pyrazolyl, oxadiazolyl, thiadiazolyl or triazyl. Examples of saturated heterocyclyl are pyrrolidinyl, tetrahydro-furanyl, piperidinyl, morpholinyl or piperazinyl.

Aryl means preferably phenyl or naphthyl.

When $R^1$ has the above-specified definition b), n is preferably 1 or 2. When $R^1$ has the above-specified definition c), n is preferably 1, 2 or 3.

The catalyst used comprises the carbonyl complexes, oxides or halides of rhenium, of manganese, of tungsten, of molybdenum, of chromium and of iron. Carbonyl complexes are understood here to mean compounds which have at least one carbonyl group as a ligand. The remaining coordination sites can be occupied by other ligands as listed by way of example in the paragraph below. Oxides and halides are also understood to mean compounds in which one or more coordination sites and/or valences are occupied by a $C_1$-$C_8$-alkyl group, and also oxyhalides. Examples thereof are $CH_3ReO_3$, $ReO_3Cl$, or $ReOCl_4$.

The catalysts may be present in all oxidation states; in the case of carbonyl complexes, they are preferably present in the 0 or I oxidation state. Preferred catalysts are the carbonyl complexes, oxides or halides of rhenium, of manganese or of molybdenum and especially of rhenium, the carbonyl complexes of rhenium or of manganese having been found to be particularly suitable.

Particularly effective carbonyl complexes are those of the abovementioned metals. One or more of the carbonyl groups may be replaced by suitable ligands such as $H_2O$, halogens, especially chlorine or bromine, phosphine ligands such as triphenylphosphine, trimethylphosphine, triethylphosphine, tri-n-butylphosphine, diphenylphosphinoethane, diphenylphosphinopropane, diphenylphosphinobutane, diphenylphosphinoferrocene, etc., amine ligands such as $NH_3$, ethylenediamine, etc., alcohol ligands such as phenol, methanol, ethanol, etc., thio ligands such as methyl mercaptan or thiophenol. Examples of suitable carbonyl complex catalysts are $Mn_2(CO)_{10}$, $Fe(CO)_5$, $Fe_2(CO)_9$, $Mo(CO)_6$, $W(CO)_6$ and $Cr(CO)_6$.

Particularly suitable catalysts have been found to be the rhenium catalysts. Examples thereof are $Re_2(CO)_{10}$, $Re(CO)_5Cl$, $Re(CO)_5Br$, $ReBr(CO)_3(CH_3CN)_2$, $ReCp(CO)_3$, $Re(pentamethyl-Cp)(CO)_3$, $ReCl(CO)_3(CH_3CN)_2$, $ReBr(CO)_3(THF)_2$, $ReCp_2$, $ReCl(CO)_3(THF)_2$, $Re_2(pentamethyl-Cp)_2(CO)_3$, $Re_2(pentamethyl-Cp)_2O_4$, $Re(pentamethyl-Cp)OCl_2$ (Cp=cyclopentadiene; THF=tetrahydrofuran), $Re_2O_7$, Re, $ReCl_3$, $ReBr_3$ and $ReCH_3O_3$. A particularly preferred catalyst is $Re_2(CO)_{10}$.

The reaction can be effected in homogeneous or heterogeneous liquid phase. When a homogeneous liquid phase is desired, a catalyst is used which is soluble in the reaction medium under the given reaction conditions or goes into solution during the reaction. Such catalysts are in particular the carbonyl complexes of the metals which are useful here. Heterogeneous catalysts are the halides and oxides of these metals, and rhenium metal. The heterogeneous catalysts can be used directly, for example in powder form, or applied to a support. Suitable supports are carbon powder, zeolites, aluminum oxides silicon oxides, etc.

In general, the catalyst is used in an amount of from 0.000005 to 1 mol %, preferably from 0.000005 to 0.5 mol %, more preferably from 0.00001 to 0.1 mol % and in particular from 0.00005 to 0.05 mol %, from 0.0001 to 0.05 mol %, from 0.0005 to 0.01 mol % or from 0.001 to 0.01 mol %, based in each case on equivalents of the compound of the formula II. The expression "equivalents" relates here to carboxyl groups of the formula II which can react with the compound of the formula III.

Suitable starting compounds of the formula II are aliphatic monocarboxylic acids. Examples of such carboxylic acids are formic acid, acetic acid, halogenated carboxylic acids, such as chloroacetic acid or trifluoroacetic acid, propionic acid, aminocarboxylic acids, such as alanine, lactic acid or butyric acid, hydroxycarboxylic acids, such as hydroxybutyric acid, valeric acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propylheptanoic acid, tertiary carboxylic acids of the formula $R^6R^7C(CH_3)COOH$ in which $R^6$ and $R^7$ are each independently $C_1$-$C_{12}$-alkyl, such as pivalic acid, 2,2-dimethylbutyric acid, 2,2-dimethylpentanoic acid, 2,2-dimethylhexanoic acid, 2,2-dimethylheptanoic acid, 2,2-dimethyloctanoic acid (Versatic acids 6, 7, 8, 9, 10), neononanoic acid, neodecanoic acid, neotridecanoic acid, stearic acid, oleic acid, lauric acid, palmitic acid, cyclohexanemono- and cyclohexanepolycarboxylic acids such as cyclohexane-carboxylic acid, cyclohexane-1,2-dicarboxylic acid, cyclohexane-1,3-dicarboxylic acid, cyclohexane-1,4-dicarboxylic acid, acrylic acid, methacrylic acid, crotonic acid, cinnamic acid or phenylacetic acid.

Suitable starting compounds of the formula II are also aliphatic polycarboxylic acids, especially dicarboxylic acids, and the derivatives of the polycarboxylic acids which have been partly esterified with a $C_1$-$C_4$-alkanol and partly amidated with ammonia, a $C_1$-$C_4$-monoalkylamine or a di-$C_1$-$C_4$-alkylamine. Examples of aliphatic polycarboxylic acids are oxalic acid, malonic acid, succinic acid, glutaric acid, adipic acid, sebacic acid, agaricic acid, 1,2,3-propanetricarboxylic acid, 1,2,3,4-butanetetracarboxylic acid, citric acid, malic acid, tartaric acid, glutamic acid, maleic acid and fumaric acid, particular preference being given to the use of adipic acid.

Suitable starting compounds of the formula II are also bicyclic mono- and dicarboxylic acids such as

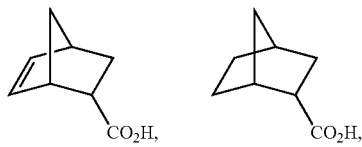

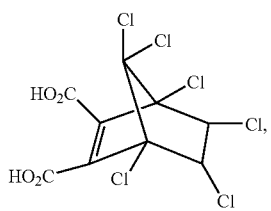

-continued

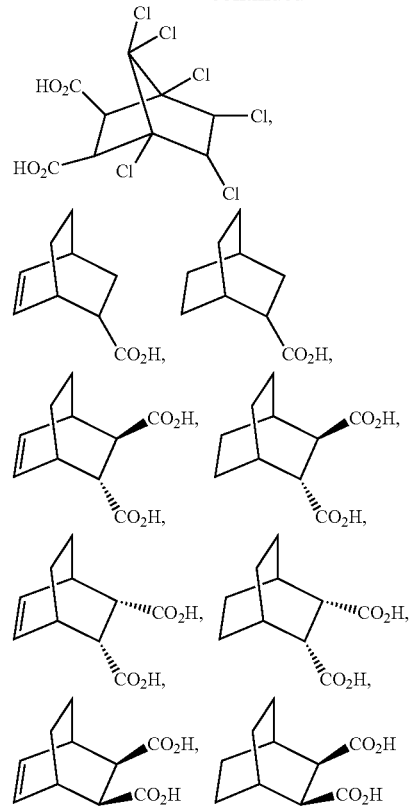

Suitable starting compounds of the formula II are also heterocyclic mono- and polycarboxylic acids and the derivatives of the polycarboxylic acids which have been partly esterified with a $C_1$-$C_4$-alkanol and partly amidated with ammonia, a $C_1$-$C_4$-mono-alkylamine or a di-$C_1$-$C_4$-alkylamine. Examples thereof are 2-pyridinecarboxylic acid, 3-pyridinecarboxylic acid or 4-pyridinecarboxylic acid, pyridinedicarboxylic acids such as 2,3- and 2,4-pyridinedicarboxylic acid, furan-2-carboxylic acid, furan-3-carboxylic acid, thiophene-2-carboxylic acid, thiophene-3-carboxylic acid or proline.

Suitable starting compounds of the formula II are also aromatic monocarboxylic acids and polycarboxylic acids and the derivatives of the polycarboxylic acids which have been partly esterified with a $C_1$-$C_4$-alkanol and partly amidated with ammonia, a $C_1$-$C_4$-monoalkylamine or a di-$C_1$-$C_4$-alkylamine. Examples of such carboxylic acids are benzoic acid, 2-, 3- or 4-methylbenzoic acid, salicylic acid, 2-, 3- or 4-aminobenzoic acid, 4-dimethylaminobenzoic acid, phthalic acid, isophthalic acid or terephthalic acid, 1,2,3-benzenetricarboxylic acid, 1,2,4-benzenetricarboxylic acid, 1,3,5-benzenetricarboxylic acid, 1,2,4,5-benzenetetracarboxylic acid, 1,2,3,4-benzenetetracarboxylic acid, benzenepentacarboxylic acid and benzenehexacarboxylic acid, and the derivatives of the polycarboxylic acids which have been partly esterified with a $C_1$-$C_4$-alkanol.

The starting compounds of the formulae II and III are commercially available or preparable by known processes. The above-described bicyclic carboxylic acids are obtainable by Diels-Alder reaction of cyclopentadiene, cyclohexadiene or cycloheptadiene with acrylic acid, maleic acid or fumaric acid, and if appropriate hydrogenation to the saturated mono- and dicarboxylic acids.

Suitable starting compounds of the formula III are, for example, acetylene, propyne, 1-butyne, 1-pentyne, 1-hexyne and phenylacetylene, particular preference being given to using acetylene.

The quantitative ratio of compound of the formula II to compound of the formula III can be selected within a wide range. In general, though, an excess of compound of the formula III is used, especially an excess of from 0.1 to 20 mol %, based on the compound of the formula II.

The reaction is generally carried out in a suitable inert solvent. If the compound of the formula II is liquid at the temperature employed, it is possible to dispense with a solvent. Suitable inert solvents are aliphatic and aromatic hydrocarbons such as pentane, hexane, heptane, decalin, paraffin oil, toluene, xylene, etc., ethers such as tetrahydrofuran, dioxane or diphenyl ether, chlorinated hydrocarbons such as methylene chloride, 1,2-dichloroethane or chlorobenzene, esters such as ethyl acetate, n-butyl acetate or butyrolactone, acetonitrile, dimethylformamide, dimethyl sulfoxide, N-methylpyrrolidone or polyethylene glycols or mixtures thereof. The reaction can also be performed in a compound of the formula I as a solvent if it is liquid at the selected reaction temperature.

The reaction temperature can be selected freely within a wide range. It is generally selected such that there is rapid conversion without starting compounds or the products decomposing. It is appropriately ≦300° C., preferably ≦260° C., more preferably ≦250° C. and in particular ≦230° C. In general, the temperature is in the range from 70 to 300° C., from 80 to 280° C., in particular from 100 to 260° C., from 100 to 250° C., from 100 to 230° C., from 100 to 210° C. or 110 to 200° C., preferably from 120 to 180° C., from 130 to 170° C., from 140 to 170° C. and especially from 150 to 170° C.

The reaction is typically carried out under pressure, preference being given to establishing from 1 to 30 bar (absolute), preferably from 2 to 20 bar and in particular from 5 to 25 bar or from 10 to 20 bar. The pressure may, for example, be established with the compound of the formula III employed and/or an inert gas such as nitrogen. The reaction time is generally in the range from 0.5 to 72 hours, especially from 1 to 48 hours.

If appropriate, it is also possible to add reaction-promoting additives such as zinc acetate, lithium salts, for example LiCl, Lewis acids such as $BF_3$, etc., Lewis bases such as triethylamine, pyridine, 1,5-diazabicyclo[4.3.0]non-5-ene, etc., substances which react with the catalyst on CO and can thus create free coordination sites, for example trimethylamino N-oxide.

The reaction can be carried out batchwise, continuously or in a semibatchwise process. The workup is effected in a customary manner, appropriately by distilling off the desired vinyl carboxylates. The catalyst remains in the bottoms and can be reused if appropriate. Appropriately, the reaction and the workup, especially the purifying distillation, can be carried out in the presence of a polymerization inhibitor. The polymerization inhibitors used may, for example, be hydroquinone, hydroquinone monomethyl ether, 2,5-di-t-butylhydroquinone, 2,6-di-t-butyl-p-cresol, nitroso compounds such as isoacryloyl nitrate, nitrosodiphenylamine, N-nitrosocyclohexyl-hydroxyamine, methylene blue, phenothiazine, tannic acid or diphenylamine. The polymerization inhibitors are used generally in amounts of from 1 to 10000 ppm, especially of from 100 to 1000 ppm, based in each case on the overall mixture.

The reaction proceeds selectively, i.e., even in the presence of other vinylatable groups in the compound of the formula II, such as OH or $NH_2$, only the carboxyl groups are vinylated. If a compound of the formula II is used which, as well as the carboxyl group(s), also comprises another vinylatable group, the reaction temperature is appropriately selected within the range from 70 to 160° C. and/or the reaction time within the range from 0.5 to 12 hours.

A preferred embodiment of the invention relates to the reaction of the compounds of the formula II in which $R^1$ is H, $C_1$-$C_6$-alkyl, $C_3$-$C_7$-cycloalkyl or phenyl, where the alkyl group may be substituted as specified above under b) and the phenyl group as specified above under c), and n is 1 with acetylene.

A further preferred embodiment relates to the reaction of the compounds of the formula II in which $R^1$ is $CO_2H$ and n is 1, or in which $R^1$ is $C_1$-$C_{20}$-alkyl, especially $C_1$-$C_4$-alkyl, where $R^1$ may be substituted as specified under b) above, and n is 2, with acetylene. Preference is given to carrying out this reaction at a temperature in the range from 70 to 220° C., preferably from 130° C. to 220° C., in particular from 140 to 180° C. or from 150 to 170° C. Catalyst is used especially in an amount of from 0.00001 to 0.1 mol %, especially from 0.0001 to 0.01 mol %, based on equivalents of dicarboxylic acid. The reaction of adipic acid with acetylene is particularly preferred.

A further preferred embodiment relates to the reaction of the compounds of the formula II in which $R^1$ is phenyl which may be substituted as defined under c) above, and n is 2, 3, 4, 5 or 6, especially 2 or 3, with acetylene. Preference is given to carrying out this reaction at a temperature in the range from 140 to 230° C., in particular from 150 to 200° C. The catalyst is used preferably in an amount of from 0.00001 to 0.1 mol %, especially from 0.0001 to 0.01 mol %, based on equivalents of polycarboxylic acid.

The present invention also provides compounds of the formula I

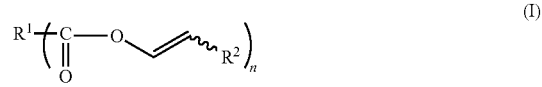

(I)

in which $R^1$ is aryl and n is 2, 3, 4, 5 or 6, where aryl is optionally substituted by 1, 2 or 3 radicals which are each independently selected from $C_1$-$C_4$-alkyl, halogen, $C_1$-$C_4$-alkoxy, amino, mono-$C_1$-$C_4$-alkylamino, di-$C_1$-$C_4$-alkylamino, —$OCOR^3$, —$COOR^3$, —$CONR^4R^5$, —$NR^4COR^5$, —$OCONR^4R^5$ or —$NR^4COOR^5$ or $R^1$ is $C_3$-$C_7$-cycloalkyl and n is 2 or 3, and $R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl.

Particular preference is given to the preparation of divinyl phthalate, divinyl terephthalate and divinyl isophthalate, and also of divinyl cyclohexane-1,2, divinyl cyclohexane-1,3 and divinyl cyclohexane-1,4, vinyl pyridine-2-carboxylate, vinyl pyridine-3-carboxylate and vinyl pyridine-4-carboxylate, and also vinyl nicotinate.

The present invention also provides the compounds of the formula I in which $R^1$ is bicycloalkyl having from 6 to 9 carbon atoms or bicycloalkenyl having from 6 to 9 carbon atoms and one or two carbon-carbon double bonds and n is 1 or 2, or in which $R^1$ is five- or six-membered heteroalkyl which has one or two heteroatoms which are each independently selected from N, O and S, where n is 1, 2 or 3; and $R^2$ is H, $C_1$-$C_8$-alkyl, phenyl-$C_1$-$C_4$-alkyl, phenyl which is optionally substituted by 1 or 2 $C_1$-$C_4$-alkyl groups, or $C_3$-$C_7$-cycloalkyl.

The vinyl esters obtainable by the process according to the invention are suitable for use in materials which can be cured thermally or by energy-rich radiation. The materials may be used as or in coating compositions, for example lacquers, printing inks or adhesives, as printing plates, as moldings, for producing photoresists, in stereolithography or as a casting material, for example for optical lenses. Substrates for the coating may, for example, be textile, leather, metal, plastic, glass, wood, paper or paperboard. The compounds of the formula I are usable as crosslinking agents in free-radical and cationic polymerizations. They are preferably used in UV-curable coatings, for example as reactive diluents.

The examples which follow illustrate the invention without restricting it. The GC analyses (GC: gas chromatography) were effected on a capillary column with a Carbowax (polyethylene glycol) film, for example DB Wax from J & W Scientific.

EXAMPLES

Example 1

A mixture of 36.0 g of benzoic acid (295 mmol), 0.25 g of $Re_2(CO)_{10}$ (0.38 mmol) and 78.0 g of toluene were subjected to vinylation at 140° C., a nitrogen pressure of 2 bar and an acetylene pressure of 18 bar for 6 h. The yield determined by GC analysis was 99%.

Example 2

A mixture of 8.0 g of adipic acid (55 mmol), 0.10 g of $Re(CO)_5Cl$ (0.28 mmol) and 17.3 g of toluene was subjected to vinylation at 140° C., a nitrogen pressure of 2 bar and an acetylene pressure of 18 bar for 6 h. The yield determined by GC analysis was 96%.

Example 3

A mixture of 8.0 g of adipic acid (55 mmol), 0.10 g of $Re(CO)_5Br$ (0.25 mmol) and 17.3 g of toluene was subjected to vinylation at 140° C., a nitrogen pressure of 2 bar and an acetylene pressure of 18 bar for 6 h. The yield determined by GC analysis was 95%.

Example 4

A mixture of 36.0 g of adipic acid (247 mmol), 0.10 g of $Re_2(CO)_{10}$ (0.15 mmol) and 78.0 g of toluene were subjected to vinylation at 140° C., a nitrogen pressure of 2 bar and an acetylene pressure of 18 bar for 6 h. The yield determined by GC analysis was 98%.

Example 5

A mixture of 300.0 g of adipic acid (2.045 mol), 1.00 g of $Re_2(CO)_{10}$ (1.50 mmol) and 700.0 g of toluene was subjected to vinylation at 160° C., a nitrogen pressure of 2 bar and an acetylene pressure of 18 bar for 6 h. The distillative workup of the reaction mixture in the presence of a polymerization inhibitor afforded the divinyl ester of the carboxylic acid in a yield of 87%.

Example 6

A mixture of 100.0 g of adipic acid (681.6 mol) and 0.50 of $Re_2(CO)_{10}$ (0.75 mmol) was heated to 200° C. without solvent for 2 h. After cooling to 160° C., the mixture was subjected to vinylation at 160° C., a nitrogen pressure of 2 bar and an acetylene pressure of 18 bar for 6 h to obtain divinyl adipate.

Example 7

A mixture of 8.0 g of terephthalic acid (48 mmol), 0.10 g of $Re_2(CO)_{10}$ (0.15 mmol) and 17.3 g of toluene was subjected to vinylation at 140° C., a nitrogen pressure of 2 bar and an acetylene pressure of 18 bar for 6 h. Divinyl terephthalate was obtained, which was detectable by means of GC-MS analysis.

Example 8

A mixture of 30.0 g (259 mmol) of fumaric acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 8 h. Divinyl fumarate was detected as the main product by means of GC-MS and GC analysis.

Example 9

A mixture of 30.0 g (181 mmol) of phthalic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 12 h. Divinyl phthalate was detected as the main product by means of GC-MS and GC analysis.

Example 10

A mixture of 30.0 g (181 mmol) of isophthalic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 20 h. Divinyl isophthalate was detected as the main product by means of GC-MS and GC analysis.

Example 11

A mixture of 30.0 g (197 mmol) of 4-methoxybenzoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 18 h. Vinyl 4-methoxybenzoate was detected as the main product by means of GC-MS and GC analysis.

Example 12

A mixture of 30.0 g (326 mmol) of pivalic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 7 h. Vinyl pivalate was detected as the main product by means of GC-MS and GC analysis.

Example 13

A mixture of 30.0 g (348 mmol) of crotonic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 6 h. Vinyl crotonate was detected as the main product by means of GC-MS and GC analysis.

Example 14

A mixture of 30.0 g (184 mmol) of 4-dimethylaminobenzoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 6 h. Vinyl 4-dimethylamino-benzoate was detected as the main product by means of GC-MS and GC analysis.

Example 15

A mixture of 30.0 g (192 mmol) of 4-chlorobenzoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 20 h. Vinyl 4-chlorobenzoate was detected as the main product by means of GC-MS and GC analysis.

Example 16

A mixture of 30.0 g (417 mmol) of acrylic acid, 0.5 g of $Re_2(CO)_{10}$ (0.77 mmol) and 90 ml of toluene was subjected to vinylation at 140° C., a nitrogen pressure of 2 bar and an acetylene pressure of 18 bar for 17 h. Vinyl acrylate was detected as the main product by means of GC-MS and GC analysis.

Example 17

A mixture of 30.0 g (149 mmol) of 4-bromobenzoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 4 h. Vinyl 4-bromobenzoate was detected as the main product by means of GC-MS and GC analysis.

Example 18

A mixture of 30.0 g (348 mmol) of methacrylic acid, 0.5 g of $Re_2(CO)_{10}$ (0.77 mmol) and 90 ml of toluene was subjected to vinylation at 140° C., a nitrogen pressure of 2 bar and an acetylene pressure of 18 bar for 13 h. Vinyl methacrylate was detected as the main product by means of GC-MS and GC analysis.

Example 19

A mixture of 40.0 g (241 mmol) of terephthalic acid, 0.5 g of $Re_2(CO)_{10}$ (0.77 mmol) and 90 ml of toluene was subjected to vinylation at 175° C., a nitrogen pressure of 2 bar and an acetylene pressure of 18 bar for 2 h. Divinyl terephthalate was detected as the main product by means of GC-MS and GC analysis.

Example 20

A mixture of 40.0 g (345 mmol) of hexanoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 1 h. Vinyl hexanoate was detected as the main product by means of GC-MS and GC analysis.

Example 21

A mixture of 40.0 g (313 mmol) of cyclohexanoic acid, 0.5 g of $Re_2(CO)_{10}$ (0.77 mmol) and 90 ml of toluene was subjected to vinylation at 160° C., a nitrogen pressure of 2 bar and an acetylene pressure of 18 bar for 3.5 h. Vinyl cyclohexanoate was detected as the main product by means of GC-MS and GC analysis.

Example 22

A mixture of 36.5 g (253 mmol) of adipic acid, 0.08 g of $Re_2(CO)_{10}$ (0.12 mmol) and 100 ml of xylene was subjected to vinylation at 160° C., a nitrogen pressure of 2 bar and an acetylene pressure of 18 bar for 24 h. Divinyl adipate was detected as the main product by means of GC-MS and GC analysis.

Example 23

A mixture of 36.5 g (253 mmol) of adipic acid, 0.08 g of $Re_2(CO)_{10}$ (0.12 mmol) and 100 ml of dioxane was subjected to vinylation at 160° C., a nitrogen pressure of 2 bar and an acetylene pressure of 18 bar for 2 h. Divinyl adipate was detected as the main product by means of GC-MS and GC analysis.

Example 24

A mixture of 36.5 g (253 mmol) of adipic acid, 0.08 g of $Re_2(CO)_{10}$ (0.12 mmol) and 100 ml of THF was subjected to vinylation at 160° C., a nitrogen pressure of 2 bar and an acetylene pressure of 18 bar for 1 h. Divinyl adipate was detected as the main product by means of GC-MS and GC analysis.

Example 25

A mixture of 36.5 g (253 mmol) of adipic acid, 0.08 g of $Re_2(CO)_{10}$ (0.12 mmol) and 100 ml of NMP was subjected to vinylation at 160° C., a nitrogen pressure of 2 bar and an acetylene pressure of 18 bar for 2.5 h. Divinyl adipate was detected as the main product by means of GC-MS and GC analysis.

Example 26

A mixture of 36.5 g (253 mmol) of adipic acid, 0.08 g of $Re_2(CO)_{10}$ (0.12 mmol) and 100 ml of diphenyl ether was subjected to vinylation at 160° C., a nitrogen pressure of 2 bar and an acetylene pressure of 18 bar for 2 h. Divinyl adipate was detected as the main product by means of GC-MS and GC analysis.

Example 27

A mixture of 6.5 g (253 mmol) of adipic acid, 0.08 g of $Re_2(CO)_{10}$ (0.12 mmol) and 100 ml of decalin was subjected to vinylation at 160° C., a nitrogen pressure of 2 bar and an acetylene pressure of 18 bar for 10 h. Divinyl adipate was detected as the main product by means of GC-MS and GC analysis.

Example 28

A mixture of 36.5 g (253 mmol) of adipic acid, 0.08 g of $Re_2(CO)_{10}$ (0.12 mmol) and 100 ml of paraffin oil was subjected to vinylation at 160° C., a nitrogen pressure of 2 bar and an acetylene pressure of 18 bar for 12 h. Divinyl adipate was detected as the main product by means of GC-MS and GC analysis.

Example 29

A mixture of 36.5 g (253 mmol) of adipic acid, 0.08 g of $Re_2(CO)_{10}$ (0.12 mmol) and 100 ml of acetonitrile was subjected to vinylation at 160° C., a nitrogen pressure of 2 bar and an acetylene pressure of 18 bar for 12 h. Divinyl adipate was detected as the main product by means of GC-MS and GC analysis.

Example 30

A mixture of 36.5 g (253 mmol) of adipic acid, 0.08 g of $Re_2(CO)_{10}$ (0.12 mmol) and 100 ml of butyrolactone was subjected to vinylation at 160° C., a nitrogen pressure of 2 bar and an acetylene pressure of 18 bar for 26 h. Divinyl adipate was detected as the main product by means of GC-MS and GC analysis.

Example 31

A mixture of 36.5 g (253 mmol) of adipic acid, 0.08 g of $Re_2(CO)_{10}$ (0.12 mmol) and 100 ml of divinyl adipate was subjected to vinylation at 160° C., a nitrogen pressure of 2 bar and an acetylene pressure of 18 bar for 24 h. Divinyl adipate was detected as the main product by means of GC-MS and GC analysis.

Example 32

A mixture of 36.5 g (253 mmol) of adipic acid, 0.05 g of $Re_2O_7$ (1.03 mmol) and 90 ml of toluene was subjected to vinylation at 160° C., a nitrogen pressure of 2 bar and an acetylene pressure of 18 bar for 6 h. Divinyl adipate was detected as the main product by means of GC-MS and GC analysis.

Example 33

A mixture of 8.0 g (56 mmol) of adipic acid, 0.10 g of rhenium powder (0.54 mmol) and 20 ml of toluene was subjected to vinylation at 160° C., a nitrogen pressure of 2 bar and an acetylene pressure of 18 bar for 6 h. Divinyl adipate was detected by means of GC analysis.

Example 34

A mixture of 36.5 g (253 mmol) of adipic acid, 0.073 g of $ReCl_3$ (0.25 mmol) and 100 ml of toluene was subjected to vinylation at 160° C., a nitrogen pressure of 2 bar and an acetylene pressure of 18 bar for 30 h. Divinyl adipate was detected as the main product by means of GC-MS and GC analysis.

Example 35

A mixture of 36.5 g (253 mmol) of adipic acid, 0.062 g of $ReCH_3O_3$ (0.25 mmol) and 100 ml of toluene was subjected to vinylation at 160° C., a nitrogen pressure of 2 bar and an acetylene pressure of 18 bar for 30 h. Divinyl adipate was detected as the main product by means of GC-MS and GC analysis.

Example 36

A mixture of 36.5 g (253 mmol) of adipic acid, 5.0 g of $Re_2O_7$ on $SiO_2/Al_2O_3$ (3% Re, 0.8 mmol) and 100 ml of toluene was subjected to vinylation at 160° C., a nitrogen pressure of 2 bar and an acetylene pressure of 18 bar for 5 h. Divinyl adipate was detected as the main product by means of GC-MS and GC analysis.

Example 37

A mixture of 18.25 g (127 mmol) of adipic acid, 0.021 g of $Re_2(CO)_{10}$ (0.03 mmol) and 60 ml of divinyl adipate was subjected to vinylation at 160° C., a nitrogen pressure of 2 bar and an acetylene pressure of 7 bar for 9.5 h. Divinyl adipate was detected as the main product by means of GC-MS and GC analysis.

Example 38

A mixture of 18.25 g (127 mmol) of adipic acid, 0.021 g of $Re_2(CO)_{10}$ (0.03 mmol) and 60 ml of divinyl adipate was subjected to vinylation at 160° C., a nitrogen pressure of 2 bar and an acetylene pressure of 4 bar for 8 h. Divinyl adipate was detected as the main product by means of GC-MS and GC analysis.

Example 39

A mixture of 18.25 g (127 mmol) of adipic acid, 0.021 g of $Re_2(CO)_{10}$ (0.03 mmol) and 60 ml of divinyl adipate was subjected to vinylation at 160° C., a nitrogen pressure of 1 bar and an acetylene pressure of 3 bar for 11 h. Divinyl adipate was detected as the main product by means of GC-MS and GC analysis.

Example 40

A mixture of 40.0 g (181 mmol) of cyclohexane-1,4-dicarboxylic acid, 0.05 g of $Re_2(CO)_{10}$ (0.08 mmol) and 90 ml of dioxane was subjected to vinylation at 160° C., a nitrogen pressure of 2 bar and an acetylene pressure of 18 bar for 5 h. Divinyl cyclohexane-1,4-dicarboxylate was detected as the main product by means of GC-MS and GC analysis.

Example 41

A mixture of 8.0 g (55 mmol) of adipic acid, 1.33 g of $Mn_2(CO)_{10}$ (3.4 mmol) and 20 ml of dioxane was subjected to vinylation at 140° C., a nitrogen pressure of 2 bar and an acetylene pressure of 18 bar for 6 h. Divinyl adipate was detected by means of GC analysis.

Example 42

A mixture of 12.0 g (82 mmol) of adipic acid, 2.00 g of $Mo(CO)_6$ (7.6 mmol) and 30 ml of toluene was subjected to vinylation at 150° C., a nitrogen pressure of 2 bar and an acetylene pressure of 18 bar for 6.5 h. Divinyl adipate was detected by means of GC analysis.

Example 43

A mixture of 8.0 g (55 mmol) of adipic acid, 1.33 g of $Fe(CO)_5$ (6.8 mmol) and 20 ml of toluene was subjected to vinylation at 140° C., a nitrogen pressure of 2 bar and an acetylene pressure of 18 bar for 6.0 h. Divinyl adipate was detected by means of GC analysis.

Example 44

A mixture of 40.0 g (171 mmol) of butanetetracarboxylic acid, 50 mg of $Re_2(CO)_{10}$ (0.08 mmol) and 80 g of xylene (isomer mixture) was subjected to vinylation at 160° C., a nitrogen pressure of 2 bar and an acetylene pressure of 18 bar for 14.0 h. Tetravinyl butanetetracarboxylate was detected by means of MS analysis.

Example 45

A mixture of 10.0 g (55 mmol) of norbornenedicarboxylic acid, 50 mg of Re$_2$(CO)$_{10}$ (0.08 mmol) and 80 g of xylene (isomer mixture) was subjected to vinylation at 160° C., a nitrogen pressure of 2 bar and an acetylene pressure of 18 bar for 4.0 h. Divinyl norbornenate was detected by means of GC analysis.

Example 46

A mixture of 15.0 g (46 mmol) of 1,4,5,6,7,7-hexachloro-5-norbornene-2,3-dicarboxylic acid (Het acid), 50 mg of Re$_2$(CO)$_{10}$ (0.08 mmol) and 15 g of xylene (isomer mixture) was subjected to vinylation at 160° C., a nitrogen pressure of 2 bar and an acetylene pressure of 18 bar for 6.0 h. Het acid divinyl ester was detected by means of GC-MS analysis.

Example 47

A mixture of 45.0 g (308 mmol) of adipic acid, 100 mg of Re$_2$(CO)$_{10}$ (0.153 mmol) and 105 g of xylene (isomer mixture) was subjected to vinylation at 200° C., a nitrogen pressure of 2 bar and an acetylene pressure of 18 bar for 9 h. Divinyl adipate was detected as the main product by means of GC analysis.

Example 48

A mixture of 7.5 g (51 mmol) of adipic acid, of 100 mg of Re$_2$(CO)$_{10}$ (0.153 mmol) and 142.5 g of xylene (isomer mixture) was subjected to vinylation at 240° C., a nitrogen pressure of 2 bar and an acetylene pressure of 18 bar for 9 h. Divinyl adipate was detected as the main product by means of GC analysis.

What is claimed is:

1. A process for preparing at least one vinyl carboxylate compound of formula I:

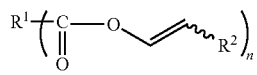
(I)

wherein
R$^1$ is

, n is 2, and
R$^2$ is H, C$_1$-C$_8$-alkyl, phenyl-C$_1$-C$_4$-alkyl, phenyl, or C$_3$-C$_7$-cycloalkyl, the process comprising:
reacting at least one starting compound selected from the group consisting of cyclohexane-1,2-dicarboxylic acid, cyclohexane-1,3-dicarboxylic acid, and cyclohexane-1,4-dicarboxylic acid,
with a compound of formula III

(III)

in the presence of at least one catalyst selected from the group consisting of a carbonyl complex of rhenium, an oxide of rhenium, a halide of rhenium, rhenium metal, a carbonyl complex of manganese, an oxide of manganese, a halide of manganese, a carbonyl complex of tungsten, an oxide of tungsten, a halide of tungsten, a carbonyl complex of molybdenum, an oxide of molybdenum, a halide of molybdenum, a carbonyl complex of chromium, an oxide of chromium, a halide of chromium, a carbonyl complex of iron, an oxide of iron, and a halide of iron, at a temperature of <300° C.

2. The process of claim 1, wherein the catalyst is at least one selected from the group consisting of a carbonyl complex of rhenium, an oxide of rhenium, a halide of rhenium, a carbonyl complex of manganese, an oxide of manganese, a halide of manganese, a carbonyl complex of molybdenum, an oxide of molybdenum, and a halide of molybdenum.

3. The process of claim 2, wherein the catalyst is Re$_2$(CO)$_{10}$.

4. The process of claim 1, wherein the catalyst is present in an amount of from 0.000005 to 1 mol % based on equivalents of the starting compound.

5. The process of claim 1, wherein the compound of formula III is selected from the group consisting of acetylene, propyne, 1-butyne, 1-pentyne, 1-hexyne, and phenylacetylene.

6. The process of claim 1, wherein the reacting is carried out at a temperature in a range from 70 to 260° C.

7. The process of claim 1, wherein the catalyst is present in an amount of from 0.000001 to 0.0025 mol %, based on equivalents of the starting compound.

8. The process of claim 1, wherein the reacting is carried out at a temperature in a range from 140 to 230° C.

9. The process of claim 1, wherein the compound of the formula III is present in the reacting in an excess of from 0.1 to 20 mol %, based on equivalents of the starting compound.

10. The process of claim 1, wherein the compound of formula III is acetylene.

11. The process of claim 1, wherein the starting compound is cyclohexane-1,2-dicarboxylic acid.

12. The process of claim 1, wherein the starting compound is cyclohexane-1,3-dicarboxylic acid.

13. The process of claim 1, wherein the starting compound is cyclohexane-1,4-dicarboxylic acid.

14. The process of claim 1, wherein the catalyst comprises at least one carbonyl complex of rhenium.

15. The process of claim 1, wherein the catalyst comprises at least one an oxide of rhenium.

16. The process of claim 1, wherein the catalyst comprises at least one halide of rhenium.

17. The process of claim 1, wherein the catalyst comprises at least one carbonyl complex of manganese.

18. The process of claim 1, wherein the catalyst comprises at least one oxide of manganese.

19. The process of claim 1, wherein the catalyst comprises at least one halide of manganese.

20. The process of claim 1, wherein the catalyst comprises at least one carbonyl complex of molybdenum.

21. The process of claim 1, wherein the catalyst comprises at least one oxide of molybdenum.

22. The process of claim 1, wherein the catalyst comprises at least one halide of molybdenum.

23. The process of claim 1, wherein the catalyst comprises at least one compound selected from the group consisting of Re, Re(CO)$_5$Cl, Re(CO)$_5$Br, Re$_2$O$_7$, ReCl$_3$, ReCH$_3$O$_3$, Mn$_2$(CO)$_{10}$, and Mo(CO)$_6$.

24. The process of claim 1, wherein the compound of formula III is propyne.

25. The process of claim 1, wherein the compound of formula III is 1-butyne.

26. The process of claim 1, wherein the compound of formula III is 1-pentyne.

27. The process of claim 1, wherein the compound of formula III is 1-hexyne.

28. The process of claim 1, wherein $R^2$ of the compound of formula I and III is a phenyl group, which is substituted by 1 or 2 $C_1$-$C_4$-alkyl groups.

29. The process of claim 1, wherein the reacting is carried out in an at least one inert solvent.

30. The process of claim 1, wherein the reacting is carried out at a temperature in a range from 150 to 170° C.

\* \* \* \* \*